United States Patent [19]

Hauck

[11] 4,082,773
[45] Apr. 4, 1978

[54] TRICYCLIC TETRAHYDRO NAPHTHALENEOLS AND RELATED COMPOUNDS

[75] Inventor: Frederic Peter Hauck, Somerville, N.J.

[73] Assignee: E. R. Squibb & Sons, Inc., Princeton, N.J.

[21] Appl. No.: 268,300

[22] Filed: Jul. 3, 1972

[51] Int. Cl.² .................... C07D 317/46; A61L 1/00
[52] U.S. Cl. .................. 260/340.5 R; 260/268 H; 260/293.55; 260/307 A; 260/326.8; 260/327 M; 260/340.2; 424/282; 544/58; 544/60; 544/59; 544/137; 544/148; 544/145; 544/79; 544/80
[58] Field of Search ........................ 260/340.5

[56] References Cited

PUBLICATIONS

Lucas, Organic Chemistry, 2nd Ed., 1953, Amer. Book Co., N.Y., pp. 460-463.
March, Advanced Organic Chemistry: Reactions, Mechanisms, and Structure, McGraw Hill, 1968, pp. 122-124.

Primary Examiner—Donald G. Daus
Assistant Examiner—James H. Turnipseed
Attorney, Agent, or Firm—Lawrence S. Levinson; Merle J. Smith; Donald J. Barrack

[57] ABSTRACT

Compounds are provided of the structure

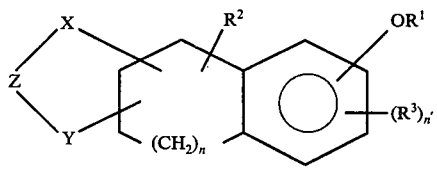

wherein X—Z—Y together with two carbons of the cycloalkyl ring form a 5- or 6-membered ring, wherein $R^1$ is hydrogen, aralkyl or acyl, $n$ is 0, 1 or 2, and $n'$ is 0, 1, 2 or 3, $R^2$ is hydrogen, lower alkyl or aralkyl, $R^3$ is hydrogen, acyl, lower alkyl, aralkyl, lower alkoxy, carboxy, halo, alkenyl, nitro, cycloalkyl, amino, acylamino, $R^2O(CH_2)_{n^2}$ where $n^2$ is 0, 1 or 2 or dihydroxyalkyl, X and Y may be the same or different and can be —$CH_2$—, =N—, —O—, —S—, —$NR^4$—, —O—$CH_2$—, —S—$CH_2$—, or —$NR^4$—$CH_2$— where $R^4$ is hydrogen, lower alkyl or aryl, Z can be

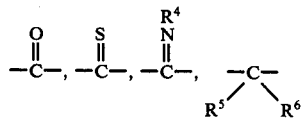

where $R^5$ and $R^6$ can be hydrogen, lower alkyl, cycloalkyl, aryl, haloalkyl, amino or substituted or unsubstituted aminoalkyl;

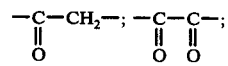

and —X—Z—Y— can be taken together to form

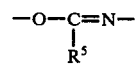

and

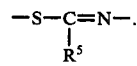

These compounds are useful as anti-fibrillatory agents, disinfectants and water-softeners.

2 Claims, No Drawings

TRICYCLIC TETRAHYDRO NAPHTHALENEOLS AND RELATED COMPOUNDS

This invention relates to compounds of the structure

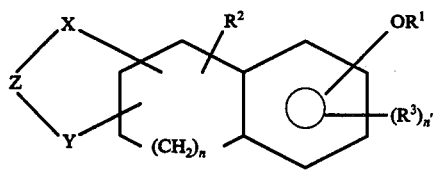

where X—Z—Y together with two carbons of the cycloalkyl ring form a 5- or 6-membered ring, wherein $R^1$ is hydrogen, aralkyl or acyl, $n$ is 0, 1 or 2, and $n^1$ is 0, 1, 2 or 3, $R^2$ is hydrogen, lower alkyl or aralkyl, $R^3$ is hydrogen, acyl, lower alkyl, aralkyl, lower alkoxy, carboxy, halo, alkenyl, nitro, cycloalkyl, amino ($R^{10}R^{11}N$), acylamino, $R^2O(CH_2)_{n^2}$ where $n^2$ is 0, 1, or 2 or dihydroxyalkyl, X and Y may be the same or different and can be —$CH_2$—, =N—, —O—, —S—, —$NR^4$—, —O—$CH_2$—, —S—$CH_2$—, or —$NR^4$—$CH_2$— where $R^4$ is hydrogen, lower alkyl or aryl, Z can be

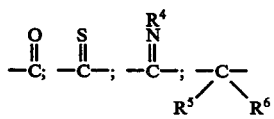

where $R^5$ and $R^6$ can be hydrogen, lower alkyl, cycloalkyl, aryl, haloalkyl, amino ($R^{10}R^{11}N$) or aminoalkyl;

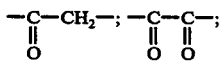

and —X—Z—Y— can be taken together to form

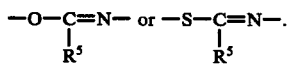

The term "lower alkyl" as employed herein includes both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like.

The term "aralkyl" includes groups such as benzyl, phenethyl as well as any of the aryl groups mentioned below attached to any of the above lower alkyl groups.

The term "lower alkoxy" includes straight and branched chain radicals of the structure RO— wherein R includes any of the above lower alkyl groups.

The "acyl" radicals are derived from hydrocarbon carboxylic acids of up to fifteen carbons and include lower fatty acid radicals such as acetyl, propionyl, butyryl, isobutyryl and the like, as well as long chain fatty acid radicals such as hexanoyl, heptanoyl, decanoyl, dodecanoyl and the like, monocyclic aryl and aralkanoic acid radicals such as benzoyl, phenacetyl and the like.

The term "monocyclic aryl" as employed herein contemplates monocyclic carbocyclic aryl radicals, for instance, phenyl and substituted phenyl radicals, such as lower alkyl phenyl (e.g., O-, m- or p-tolyl, ethylphenyl, butylphenyl and the like, di(lower alkyl)phenyl (e.g., 2,4-dimethylphenyl, 3,5-diethylphenyl and the like), halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl and the like), trinitrophenyl (e.g., picryl), and alkoxyphenyl such as methoxyphenyl.

The terms "monocyclic cycloalkyl" includes cyclic radicals containing from 3 to 6 ring members (e.g., cyclopropyl, cyclobutyl, cyclopentyl and cyclohexyl).

The term "alkenyl" includes monounsaturated groups containing three to eight carbons such as allyl, and any of the isomers of butenyl, pentenyl, hexenyl, heptenyl and octenyl.

The term "halogen" includes F, Br, Cl or I.

Alkyl radicals substituted by one halogen atom suchas F, Br, Cl or I are encompassed by the term halolower alkyl.

The amino groups are basic nitrogen containing radicals

$R^{10}$ and $R^{11}$ each represents hydrogen, lower alkyl, lower alkenyl, hydroxy-lower alkyl, acyl, and phenyl-lower alkyl forming such basic groups as amino, lower alkylamino, e.g., methylamino, ethylamino, isopropylamino, di(lower alkyl)amino, e.g., dimethylamino, diethylamino, dipropylamino, lower alkenylamino, e.g., allylamino, di(lower alkenyl)amino, e.g., diallylamino, (hydroxy-lower alkyl)-amino, e.g., hydroxyethylamino, di(hydroxy-lower alkyl)amino, e.g., di(hydroxyethyl)amino, phenyl(loweralkyl)amino, e.g., benzylamino, phenethylamino, N-(lower alkyl)-phenyl(lower alkyl)amino, e.g., N-methylbenzylamino, and the like.

The

radical may form a heterocyclic radical. The symbols $R^{10}$ and $R^{11}$ may together represent the carbon (and hydrogen) and the oxygen, sulfur or nitrogen atoms which, with the nitrogen or carbon atom in the above group, form a 5- or 6-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinbefore; trifluoromethoxy; trifluoromethylmercapto; N,N-dialkylsulfamoyl groups, such as N,N-diemthylsulfamoyl; lower alkanoyl groups

where R is lower alkyl) as defined hereinbefore, such as acetyl, propionyl, and the like; hydroxy-lower alkyl, such as hydroxymethyl,2-hydroxyethyl or the like; hydroxy-lower alkoxy-lower alkyl, such as 2-(2-hydroxyethoxy)ethyl, or the like; lower alkanoyl-lower alkyl, such as 2-heptanoyloxyethyl; carbo-lower alkoxy, such as carbomethoxy, carboethoxy, carbopropoxy, or the like; or 2-(lower alkanoyloxy-lower alkoxy)lower alkyl such as 2-decanoyloxyethoxy)ethyl, or the like.

Illustrative of the heterocyclic radicals represented by

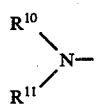

are the following: piperidino; (lower alkyl)piperidino [e.g., 2-, 3-, or 4-lower alkyl)piperidino or 4-(N-lower alkyl)piperidino, such as 2-(ethyl)piperidino or 4-(N-isopropyl)piperidino]; di(lower alkyl)piperidino [e.g., 2,4-, 2,5- or 3,5-di(lower alkyl)piperidino, such as 2,4-dimethyl piperidino or 2,5-di-t-butyl piperidino]; (lower alkoxy)piperidino [e.g., 2-methoxypiperidino or 3-methoxypiperidino]; hydroxypiperidino [e.g., 3-hydroxy- or 4-hydroxypiperidino]; aminomethyl-piperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino, [e.g., 3,5-dimethylmorpholino]; (lower alkoxy)morpholino, [e.g., 2-methoxymorpholino]; thiamorpholino; (lower alkyl)thiamorpholino [e.g., 3-methylthiamorpholino]; di(lower alkyl)thiamorpholino, [e.g., 3,5-dimethylthiamorpholino], (lower alkoxy)thiamorpholino, [e.g., 3-methoxythiamorpholino]; piperazino; (lower alkyl)piperazino, [e.g., $N^4$-methylpiperazino]; di(lower alkyl)piperazino, [e.g., 2,5-dimethylpiperazino or 2,6-dimethylpiperazino]; (lower alkoxy)piperazino, [e.g., 2-methoxypiperazino]; (hydroxy-lower alkyl)-piperazino, [e.g., $N^4$-(2-hydroxyethyl)piperazino]; (lower alkanoyloxy-lower alkyl)piperazino, [e.g., $N^4$-(2-heptanoyloxyethyl)piperazino or $N^4$-(2-propionyloxyethyl)piperazino]; (hydroxy-lower alkoxy-lower alkyl)-piperazino, [e.g., (hydroxymethoxymethyl)piperazino]; (carbo-lower alkoxy)piperazino, [e.g., $N^4$-(carbomethoxy-, carboethoxy-, or carbopropoxy)piperazino]; piperidyl; (lower alkyl)piperidyl [e.g., 1-, 2-, 3- or 4-(lower alkyl)piperidyl, such as 1-N-methylpiperidyl or 3-ethylpiperidyl]; di(lower alkyl)piperidyl, [e.g., 2,4-, 2,5-, or 3,5-di(lower alkyl)piperidyl wherein lower alkyl is methyl, ethyl, n-propyl, isopropyl, etc.]; lower alkoxy piperidyl, [e.g., 3-methoxypiperidyl or 2-ethoxypiperidyl]; hydroxypiperidyl [e.g., 3-hydroxy- or 4-hydroxypiperidyl]; aminomethylpiperidyl, [e.g., 4-aminoethylpiperidyl]; pyrrolidyl; lower alkyl pyrrolidyl, [e.g., 1-N-methylpyrrolidyl]; di(lower alkyl)pyrrolidyl, [e.g., 2,3-dimethylpyrrolidyl]; lower alkoxy pyrrolidyl, [e.g., 4-N-methoxypyrrolidyl]; morpholinyl; (lower alkyl)-morpholinyl, [e.g., 3-methylmorpholinyl]; di(lower alkyl)morpholinyl, [e.g., 3-methyl-4-N-ethylmorpholinyl]; (lower alkoxy)morpholinyl, [e.g., 2-ethoxymorpholinyl]; thiamorpholinyl; (lower alkyl)thiamorpholino, [e.g., 3-ethylthiamorpholinyl]; di(lower alkyl)thiamorpholinyl, [e.g., 3-methyl-4-N-ethylthiamorpholinyl]; lower alkoxy thiamorpholino, [e.g., 3-methoxythiamorpholinyl]; piperazinyl; alkyl, dialkyl, alkoxy or hydroxy-lower alkyl substituted piperazinyl.

The compounds of formula I where X, Y, Z or $R^3$ includes a basic nitrogen form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, oxalate, tartrate, maleate, citrate, succinate, benzoate, ascorbate, salicylate, methanesulfonate, benzenesulfonate, toluenesulfonate and the like. Quaternary ammonium salts are also formed, e.g., by reacting the free base with an alkylating agent, e.g., lower alkyl halide such as methyl chloride, ethyl bromide or the like, lower alkyl sulfate such as methyl sulfate, aralkyl halides such as benzyl chloride, aralkyl sulfates such as benzyl sulfate and the like.

Preferred are those compounds wherein $n$ is 1, X is O, Y is O and Z is $CH_3$—C—$CH_3$, $R^2$ is hydrogen, $R^1$ is hydrogen and $OR^1$ is at the 1-position and $R^3$ is hydrogen.

The —X—Z—Y group will be attached to the cycloalkyl ring on two vicinal carbon atoms.

Compounds of formula I wherein X and Y are O or one of X and Y is O and the other —S— and Z is

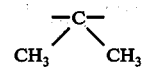

that is

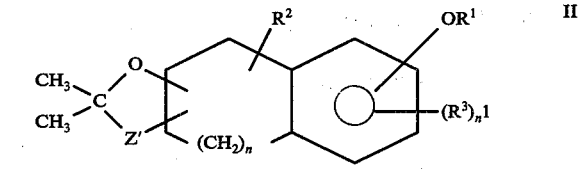

where Z' is —O— or —S—, can be prepared by reacting a compound of the structure.

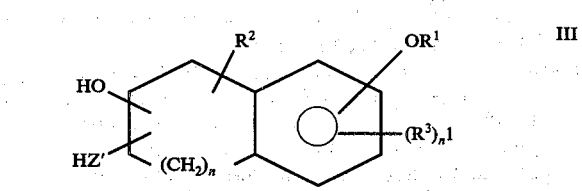

where Z' is —O— or —S—, with dimethoxypropane in the presence of p-toluene sulfonic acid.

Compounds of formula I wherein X and Y are —O— or one of X and Y is —O— and the other —S— and Z is

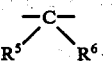

that is

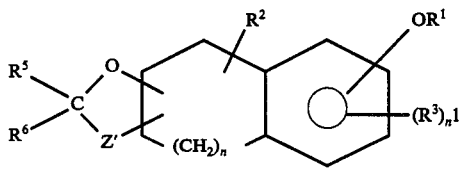  IV can be prepared by reacting an aldehyde or ketone of the structure

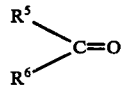  V with a compound of structure III in the presence of an aromatic hydrocarbon solvent, such as benzene, and p-toluene sulfonic acid.

Compounds of the structure I where one of $R^5$ and $R^6$ is haloalkyl and the other hydrogen, that is

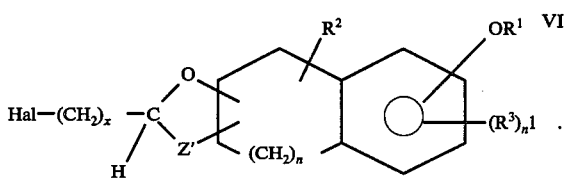  VI where $x$ is 1 to 5 and $Z'$ is —O— or —S—, can be prepared by reacting a compound of the structure III with a dialkoxy alkyl halide of the structure.

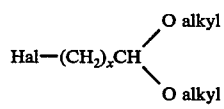  VII such as

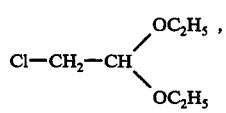

in the presence of p-toluene sulfonic acid.

The above haloketal can be reacted with an amine of the structure

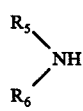  VIII in the presence of a lower alkanol such as methanol or ethanol to form compounds of the structure

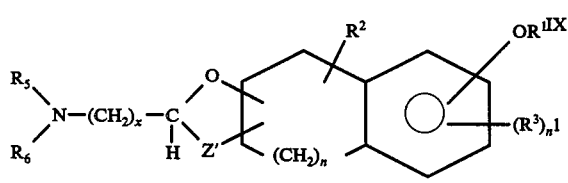  IX

Compounds of the structure

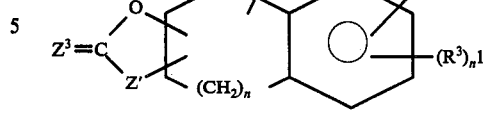  X can be prepared by reacting a diol of the structure

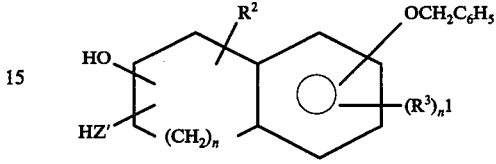  XI where $Z'$ is —O— or —S—, with phosgene or ethyl chloroformate or with N,N'-carbonyldiimidazole where $Z^3$ is O or with thiophosgene where $Z^3$ is S.

Compounds of the structure I wherein X and Y are O and Z is

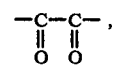

that is

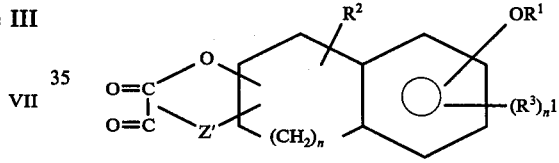  XII can be prepared by acylating a compound of structure III with oxalyl chloride and a basic solvent such as pyridine.

Compounds of the structure I wherein X and Y are O and Z is

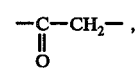

that is

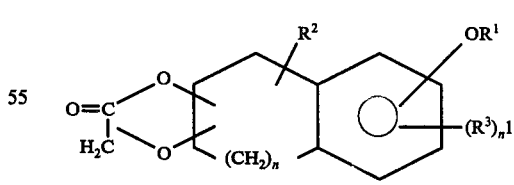  XIII can be prepared by reacting a compound of the structure III with a halo ester of the structure Hal—CH$_2$CO$_2$alkyl     (XIV)

such as Cl—CH$_2$CO$_2$C$_2$H$_5$, and an alkali metal hydride such as sodium hydride.

Compounds of the structure I wherein X is —O—, Y is —N$_R$—$_4$ and Z is C≡Z', that is

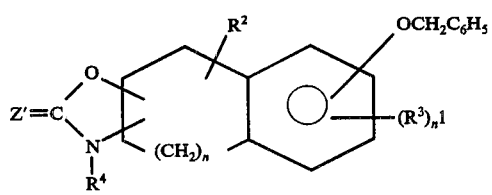

Where Z' is O= or S=, can be prepared by reacting a compound of the structure

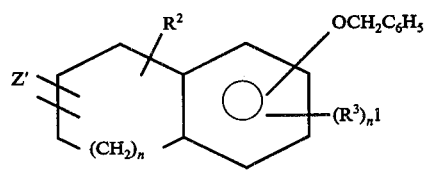

prepared as described hereinafter, with an isocyanate or isothiocyanate compound of the structure

    (XVII)

or

    (XVIII)

respectively, such as phenyl isocyanate or butylisocyanate, or the corresponding isothiocyanates, in the presence of tributyl phosphine oxide and lithium bromide, in an aromatic solvent such as xylene, as outlined in Tetrahedron Letters 809 (1971).

Compounds of the structure I where —X—Z—Y— are taken together to form

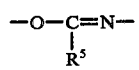

or

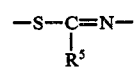

where $R^5$ is

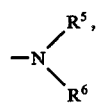

that is

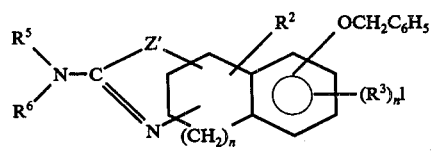

where Z' is O or S, can be prepared by reacting a compound of the structure

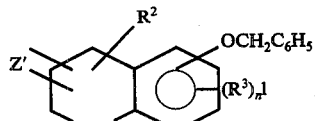

with a compound of the structure

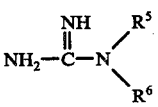

such as guanidine, cyanamide guanidine or alkyl or arylguanidine, (Aeta Pol. Pharm. 28 151 (1971), Index Chem. 178179).

trans Oxazolines, that is compounds of the structure I, wherein —X—Z—Y— are taken together to form

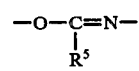

where $R^5$ is aryl, that is

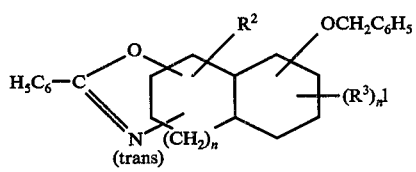

can be prepared by reacting a trans amino alcohol of the structure

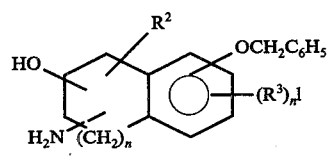

prepared as described in copending application Ser. No. 268,314 filed July 3, 1972, now abandoned entitled "Substituted Cyclic Polymethylene Phenols" with ethyl iminobenzoate, as per the procedure described in JACS 72 2187 (1950).

cis Oxazolines, that is compounds of the structure I wherein —X—Z—Y are taken together to form

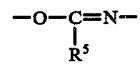

where $R^5$ is aryl, that is

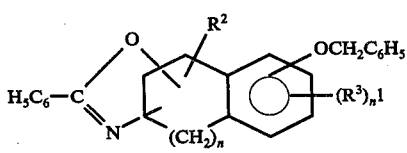

can be prepared by converting the above trans amino alcohol of structure XXIII to its N-benzoyl derivative by reacting it with benzoyl chloride in pyridine and reacting the benzoyl chloride with thionyl chloride.

Compounds of structure I wherein X is —O—, or —N—, Y is —CH$_2$— and Z is C=O that is

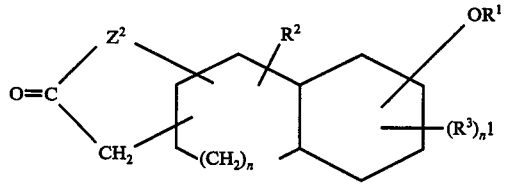

where Z$^2$ is —O—, or —S—, can be prepared as follows: a compound of the structure

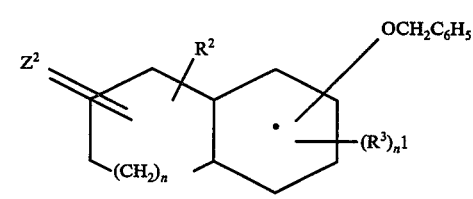

is reacted with diethyl malonate to form

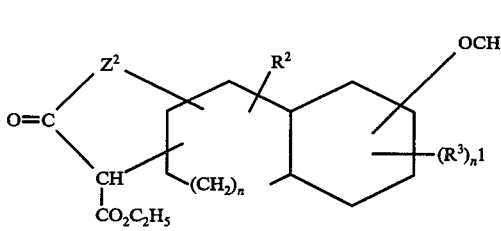

which is hydrolyzed in the presence of an acid to form

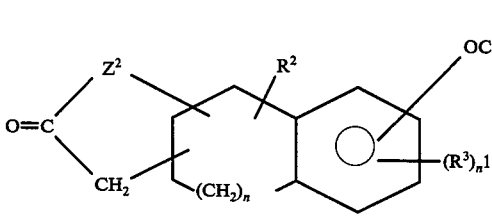

Compounds of formula I which include R$^3$ substituents on the aromatic ring can be prepared in a variety of ways depending on the nature of the specific R$^3$ substituent.

Those substituents such as lower alkyl, cycloalkyl, non-conjugated alkenyl and lower alkoxy stable to the conditions of a Birch reduction procedure may be present in the indanol, naphthol, or benzosuberaneol precursor.

Those substituents not stable to the conditions of the Birch reduction can be introduced at a later stage by wellknown aromatic substitution reactions on suitably protected tetrahydronaphthols or benzosuberaneols or indanols. Thus, for example, acetals of structure XXIX below can be alkylated with benzyl halides in aqueous base to yield arylalkyl derivatives of structure XXX, halogenated in solvents such as carbon tetrachloride to give XXXI, or nitrated with nitric acid in acetic acid to give XXXII.

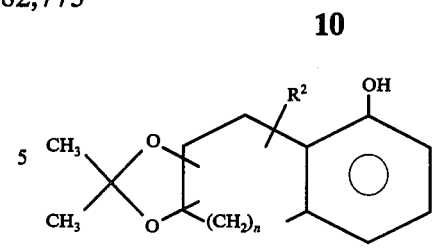

XXIX

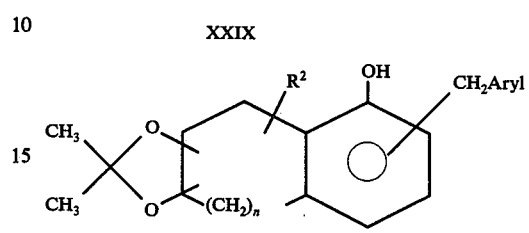

XXX

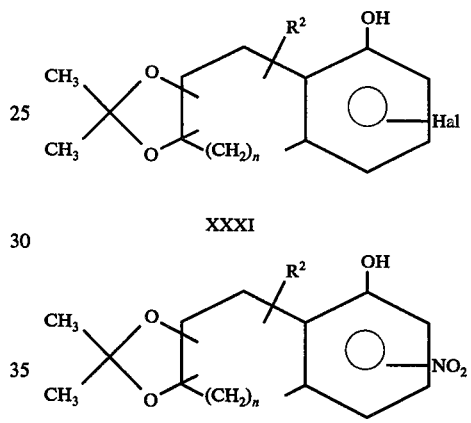

XXXI

XXXII

Compound XXIX can also be converted to the corresponding acyl derivative XXXIII with the appropriate anhydride in pyridine as described hereinbefore; subjecting compound XXXIII to a Fries rearrangement provides the acyl compounds XXXIV which are easily reduced to the corresponding hydroxyalkyl compound XXXV.

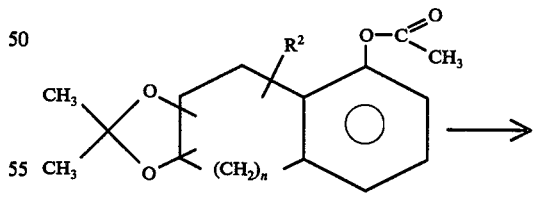

XXXIII

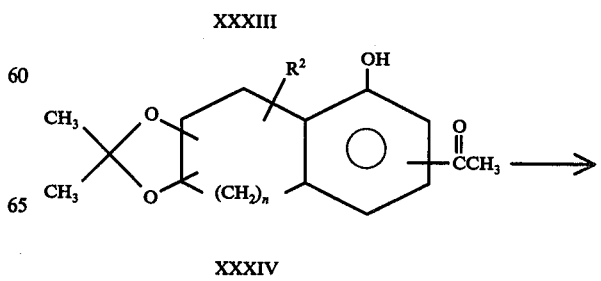

XXXIV

-continued

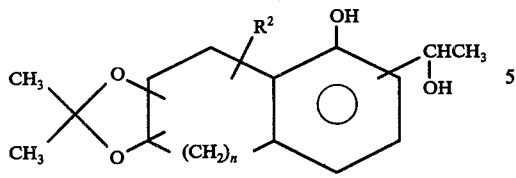

XXXV

Conversion of XXIX to the corresponding alkenyl ether XXXVI by alkylation with an allyl halide and base in a suitable solvent such as DMSO followed by a Claisen rearrangement in dimethylaniline provides alkenyl compounds of structure XXXVII which can be converted to mono- and dihydroxyalkyl derivatives with appropriate well-known oxidizing agents, such as peracids.

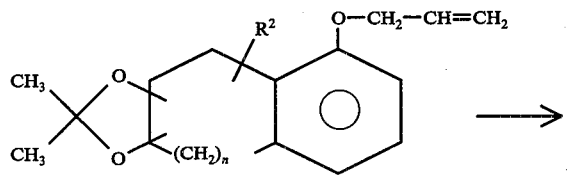

XXXVI

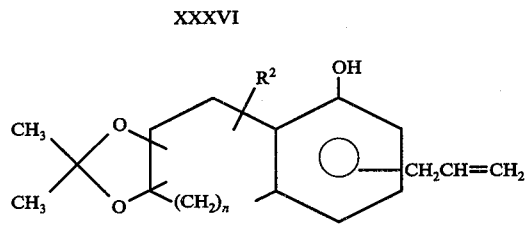

XXXVII

In the above cases, the protecting ketal function can be removed by hydrolysis in dilute acid to yield the corresponding diol.

Similar cyclic derivatives of other vicinally substituted tetrahydronaphthols, indanols or benzosuberaneols as described herein may be employed in like manner to protect the functionality during aromatic substitution. Alternatively, acyl derivatives such as acetyl may be employed in place of cyclic derivatives.

The phenol or phenol derivative starting materials of the structure

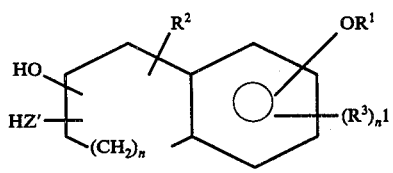

III where Z' is —O— or —S— or

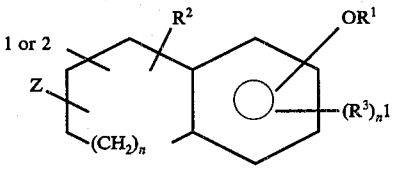

IIIA where $Z^{1 \, or \, 2}$ is —O— or —S— or —N— are described in detail in copending application Ser. No. 203,865, filed Dec. 1, 1971, now U.S. Pat. No. 3,935,267 entitled "Tetrahydronaphthyloxy-Aminopropanols and Related Compounds," and in copending application Ser. No. 268,314, filed July 3, 1972, now abandoned entitled "Substituted Cyclic Polymethylene Phenols."

It will be appreciated that compounds of the invention wherein the $OR^1$ group is in the 2-position or $\beta$-position may be prepared as described hereinbefore with respect to the compounds of the invention wherein $OR^1$ is in the 1- or $\alpha$-position, employing as starting materials, compounds where $OR^1$ is in the 2- or $\beta$-position.

The new compounds of this invention are useful as water softeners and for inhibiting the corrosivity of engine lubricants.

They are also useful as antifibrillatory agents, for example, in arresting cardiac arrhythmia in mammals, e.g., by inhibition of beta adrenergic receptors in the myocardium, as well as in lowering blood pressure and central nervous system depressants. For these purposes a compound of formula I or a physiologically acceptable acid addition salt may be incorporated in a conventional dosage form such as tablet, capsule, elixir, injectable or the like along with the necessary carrier material, excipient, lubricant, buffer or the like. Single or divided doses of about 5 to 25 mg/kg/day, preferably about 4 to 10 mg/kg, two to four times daily may be administered in dosage forms as described above.

In addition, the compounds of the invention may be used as surface disinfectants. About 0.01 to 1 percent by weight of any of these substances may be dispersed on an inert solid or in a liquid such as water and applied as a dust or spray. They may be incorporated also, for example, in a soap or other cleansing agent, e.g., a solid or liquid detergent, detergent composition, for example, in general cleaning, in cleaning dairy barns or equipment or cleaning food handling or processing equipment.

The following examples illustrate the present invention without, however, limiting the same thereto. All temperatures are expressed in ° C.

EXAMPLE 1

Acetonide of cis-5,6,7,8-tetrahydro-1,6,7-naphthalene-triol

A. cis-5,6,7,8-Tetrahydro-1,6,7-naphthalenetriol

A solution of 29.2 g. (0.2 mole) of 5,8-dihydro-1-naphthol and 40 ml. of acetic anhydride in 100 ml of pyridine is prepared. After 16 hr. the solvent is removed in vacuo and the residue dissolved in ether and washed with 200 ml. of 5% hydrochloric acid, water, 200 ml. of 10% sodium hydroxide, saturated salt solution and dried. Solvent removal gives 34.2 g (90.5%) of crude acetate which is dissolved in 900 ml. of acetic acid and 36 ml. of water. 53.3 g. (0.32 mole) of silver acetate is added followed by 40.6 g. (0.16 g-atom) of iodine. The slurry is heated with good stirring at 85± 10° for 3 hr. under nitrogen, cooled and filtered. The filtrate is evaporated in vacuo and the residue dissolved in 250 ml. of methanol and cooled to 0°. A solution of 40 g. of sodium hydroxide in 200 ml. of water is added under nitrogen and the mixture stirred overnight. The bulk of the methanol is removed in vacuo whereupon a solid forms. The solid is separated by filtration, dissolved in 150 ml. of water and acidified with 20 ml. of concentrated hydrochloric acid. Cooling gives a solid which is filtered and dried to give 16.5 g. 2,3 cis-5,6,7,8-tetrahydro-1,6,7-naphthalenetriol m.p. 184.5–187°. Three recrystallizations from absolute ethanol give the analytical sample, m.p. 188°–188.5°.

Anal. Calc'd for $C_{10}H_{12}O_3$: C, 66.65; H, 6.71; Found: C, 66.19; H, 6.68.

B. Acetonide of cis-5,6,7,8-tetrahydro-1,6,7-naphthalene-triol

A slurry of 5.4 g of the cis-5,6,7,8-tetrahydro-1,6,7-naphthalene-triol in 50 ml of 2,2-dimethoxy propane is treated with 150 mg. of TsOH (solution in 10 min). After 1 hr. the solution is partitioned between ether and sat'd bicarbonate solution. The organic layer is dried and evaporated to give 6.58 g. essentially TLC homogeneous. Crystallization of a small sample from hexane/ethyl acetate gives the title material of mp. 130.5°–131.5°.

EXAMPLE 2

$O^6,O^7$-Butylidene-5,6,7,8-tetrahydro-1,6,7-naphthalenetriol

A solution of 3.6 g (0.02 moles) of the triol of Example 1-A in 50 ml. of benzene, and 1.5 g of butanal in the presence of 0.1 g p-toluene sulfonic acid are mixed together and stirred for several hrs. Water is removed by azeotropic distillation and the residue is taken to dryness to yield the title compound.

EXAMPLE 3

$O^6,O^7$-β-Diethylaminoethylidene-5,6,7,8-tetrahydro-1,6,7-naphthalenetriol

A. 6,7-β-chloroethylidene-5,6,7,8-tetrahydro-1,6,7-naphthalenetriol

A solution of 27 g (0.15 moles) of cis-5,6,7,8-tetrahydro-1,6,7-naphthalenetriol prepared as described in Example 1 in 250 ml of benzene and 25 g of diethoxyethyl chloride in the presence of 0.2 g p-toluene sulfonic acid are mixed together for several hours. Water is removed by azeotropic distillation and the residue taken to dryness to yield the title compound.

B. $O^6,O^7$-β-Diethylaminoethylidene-5,6,7,8-tetrahydro-1,6,7-naphthalenetriol The procedure described in J. Pharm and Pharmac. 23, 649 (1971) is followed.

The haloacetal from part A is dissolved in ethanol containing excess diethylamine and the mixture heated at 100° C for 48 hours in a bomb. The mixture is cooled and water and solvent stripped therefrom. The residue is purified by chromatography on Alumina II neutral to yield the title compound.

EXAMPLE 4

5,6,7,8-tetrahydro-1,6,7-naphthalenetriol-$O^1$-benzylether-$O^6,O^7$-carbonate

A. 5,8-Dihydro-1-naphthol, benzyl ether

A solution of 5,8-dihydro-1-naphthol (73 g., 0.5 M) in 400 ml. DMSO is treated with 0.5 M of sodium methoxide. The mixture is cooled in an ice bath while benzyl bromide (85.5 g., 0.5 M) is added dropwise. The mixture has to be shaken periodically since there is difficulty in stirring. Toward the end of the addition the mixture is allowed to warm to ~45°, and stirring is continued for 2–3 hours after addition is complete. The mixture is then poured into 1 liter $H_2O$ and the product is extracted into ether. The ether extracts are washed with 10% NaOH, dried and the solvent is removed in vacuo to give a quantitative yield of crude crystalline product.

A small sample (4 g.) of this is recrystallized twice from methanol to give the title compound, 1.3 g., mp 70°–74°.

Anal. Calc'd for $C_{17}H_{16}O$: C, 86.40; H, 6.83 Found: C, 86.58; H, 6.6

B. cis-5,6,7,8-tetrahydro-1,6,7-naphthalenetriol-$O'$-benzyl ether

To 47.2 g (0.20 mole) of the above ether dissolved in 900 ml of acetic acid containing 30 ml of water is added 53.3 g (0.32 mole) of silver acetate with vigorous stirring followed by 40.6 g (0.16 g. atom) of iodine. After 1 hour, the slurry is heated to 85–95° for 3 hours under nitrogen, cooled and filtered. The filtrate is taken to dryness in vacuo and the residue taken up in 250 ml of methanol and treated in the cold with a solution of 40 g of sodium hydroxide in 200 ml of water. After stirring overnight, the bulk of the methanol is removed in vacuum, and the product extracted into chloroform. After drying and solvent removal, the product is induced to crystallize by triturating with hexane.

C. 5,6,7,8-tetrahydro-1,6,7-naphthalenetriol-$O'$-benzylether-$O^6,O^7$-carbonate In accordance with the procedure set out in Arch. Pharm. 304 590 (1971), a solution of 27 g (0.1 mole) of the diol N,N-carbonyl diimidazole and heated under reflux for 2 hrs. After cooling, the mixture is poured into water and the product extracted into $CHCl_3$, dried and purified on deactivated silica gel to give the title compound.

EXAMPLE 5

$O^6,O^7$-2'-Butylidene-5,6,7,8-tetrahydro-2,6,7-naphthalenetriol

A. 5,8-Dihydro-2-naphthol

The procedure of Marshall, et al, Can. J. Chem., 47. 3127 (1969) is followed exactly. From 25.0 g of β-naphthol is obtained 18.9 g of crude product. NMR analysis indicated it to contain ca. 40% of the desired 5,8-dihydro-2-naphthol and 60% of 5,6,7,8-tetrahydro-2-naphthol.

B. cis-5,6,7,8-Tetrahydro-2,6,7-naphthalene triol

The 18.9 g. of crude product was converted to the acetate by the procedure used in Example 1 and the resulting oil (23.8 g) was heated at 90° for 3 hr. with 300 ml. of acetic acid, 20 ml. of water, 23.5 g. of silver acetate and 18.0 g. of iodine. The slurry was cooled and filtered. The filtrate was evaporated and the residue stirred overnight under nitrogen with 100 ml. each of water and methanol and 20 g. of sodium hydroxide. The methanol was removed in vacuo and the residue acidified at 0° with 155 ml. of 12% hydrochloric acid. The oil which separated crystallized when shaken in a separatory funnel with chloroform. Filtration gave 7.9 g. of tan solid. Recrystallization from ethanol/ethyl acetate gave in several crops 4.03 g., mp 193°–195.5°.

C. $O^6,O^7$-2'-butylidene-5,6,7,8-tetrahydro-2,6,7-naphthalenetriol

Following the procedure of Example 2 substituting for butanal, methyl ethyl ketone, the title compound is obtained.

EXAMPLE 6

Acetonide of 7(and 6)mercapto-5,6,7,8-tetrahydronaphthalene-1,6(and 7)diol

A. 6,7-Epoxy-5,6,7,8-tetrahydro-1-naphthyl benzyl ether

A solution of 73 g. (0.5 m) of 5,8-dihydro-1-naphthol in 100 ml. DMSO is treated with 0.5 m sodium methoxide. The mixture is cooled in an ice bath and treated dropwise with 0.5 mole benzyl bromide with shaking periodically. The mixture is gradually allowed to warm up to about 45° toward the end of addition. The mixture is stirred 3 hrs. longer, then poured into 1 liter $H_2O$ and extracted into ether. Extracts are washed twice with 10% NaOH, dried, taken to dryness leaving almost a quantitative yield of crystalline 5,8-dihydro-1-naphthyl benzyl ether.

A solution of 23.6 g. (0.10 m) of the above ether in 250 ml. $CHCl_3$ is treated with a solution of 0.11 m m-chloroperbenzoic acid in $CHCl_3$ at 10°–15° C and stirred overnight. After filtration, the organic filtrate is washed with dilute $K_2CO_3$, dried and freed of solvent, leaving crude solid epoxy ether.

B. 7(and 6)Mercapto-5,6,7,8-tetrahydronaphthalene-1,6(and 7)diol

A solution of the above epoxyether (12.6 g, 0.05 m) in ethanol was added to an aqueous solution of sodium sulfide and the resulting mixture warmed for several hours. After cooling and acidification with acetic acid, the product was extracted into $CHCl_3$, dried and freed of solvent to leave a mixture of isomeric mercapto alcohols of structure:

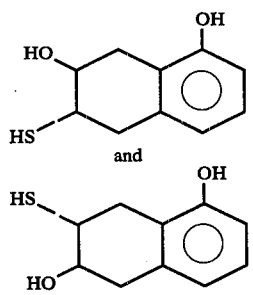

C. Acetonide of 7(and 6)mercapto-5,6,7,8-tetrahydronaphthalene-1,6(and 7)diol In a manner similar to Example 1B, substituting the above mercapto compounds from part E for the triol, the title acetonide is obtained.

EXAMPLE 7

S,$O^7$-2'-Hexylidene-6-mercapto-5,6,7,8-tetrahydronaphthalene-1,7-diol

Employing the mercaptan prepared in Example 6B in lieu of the 1,2,3,4-tetrahydro-1,2,5-naphthalenetriol in the procedure of Example 2, and replacing the butanal with methyl butyl ketone, the following compound is obtained

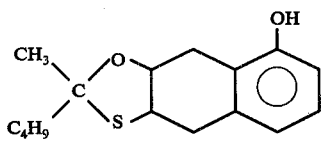

EXAMPLE 8

S,$O^7$-β-Chloroethylidene-6-mercapto-5,6,7,8-tetrahydronaphthalene-1,7-diol

Employing the mercaptan prepared in Example 6B in lieu of cis-5,6,7,8-tetrahydro-1,6,7-naphthalenetriol in the procedure of Example 3, the following compound is obtained

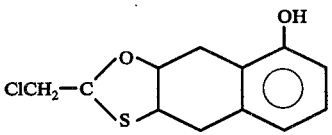

EXAMPLE 9

6-Mercapto-5,6,7,8-tetrahydronaphthalene-1,7-diol S,$O^7$-carbonate-$O'$-benzyl ether Employing the benzyl ether of the mercaptan of Example 6B in the procedure of Example 4 in lieu of the diol, the following compound is obtained

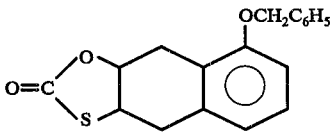

EXAMPLE 10

7(and 6)Hydroxy-5,6,7,8-tetrahydro-6(and 7)-naphthyloxyacetic-acid lactone

The above compound is prepared by reacting 0.1 mole 5,6,7,8-tetrahydro-1,6,7-naphthalenetriol $O'$-benzyl ether with 0.1 mole of Cl-$CH_2CO_2C_2H_5$ in 100 ml of dimethoxyethane in the presence of 3 g NaH and heating the mixture at reflux for several hours and thereafter separating the product from the reaction mixture by chromatography on silica gel.

Catalytic debenzylation over 5% Pd/c in ethanol then affords the free phenol.

EXAMPLE 11

5,6,7,8-tetrahydronaphthalene-1,6,7-triol $O^6,O^7$-cyclic oxalate-$O'$-benzyl ether The above compound is prepared by dissolving 0.1 m of 5,6,7,8-tetrahydro-1,6,7-naphthalenetriol $O'$-benzyl ether in 25 ml of cold pyridine and adding 0.1 m of oxalyl chloride dropwise. After filtration and solvent removal, the product is purified by chromatography on silica gel. Catalytic debenzylation over 5% Pd on C then yields the free phenol.

EXAMPLE 12

6-Mercapto-5,6,7,8-tetrahydro-naphthalene-1,7-diol-$O'$-benzyl ether $O^7$,S-thiocarbonate The procedure of Examples 9 and 4 are followed employing the benzyl ether of the mercaptan of Example 6B and thiophosgene in place of phosgene to form the above compound.

EXAMPLE 13

6-Amino-5,6,7,8-tetrahydronaphthalene-1,7-diol-$O'$-benzyl ether $O^7$,N-carbonate A solution of 0.1 m each of the epoxide benzyl ether of Example 6A and phenyl isocyanate in xylene is added to a solution containing 0.004 m of tributyl phosphine oxide and 0.003 m of lithium bromide in xylene and the mixture heated under reflux overnight. After cooling, solvent is removed and the crude mixture of products purified on neutral Alumina III to give the title compound.

Method Ref. Tet. Letters 809 (1971)

EXAMPLE 14

6-Amino-5,6,7,8-tetrahydronaphthalene-1,7-diol-$O'$-benzyl ether $O^7$,N-thiocarbonate A solution of 0.1 m each of the epoxide benzyl ether of Example 6A and butylisothiocyanate in xylene added to a solution containing 0.004 m of tributyl phosphine oxide and 0.003 m of lithium bromide in xylene and the mixture heated under reflux overnight. After cooling, solvent is removed and the crude mixture of products purified on neutral Alumina III to give the title compound.

Method Ref. Tet. Letters 809 (1971).

EXAMPLE 15

C-Phenylimidazole derivative of 6-Amino-5,6,7,8-tetrahydronaphthalene-1,7-diol $O'$-benzyl ether A. 6,7-Epoxy-5,6,7,8-tetrahydro-1-naphthol benzyl ether A solution of 12.8 (0.054 m) of 5,7-dihydro-1-naphthol benzyl ether in 150 ml of $CH_2Cl_2$ was cooled to 0° and 8.9 g 0.052 mole of m-chlorobenzoic acid was added over a period of 5 min. and the mixture was stirred overnight at room temperature.

The suspension was poured into a mixture of 50 ml of 10% NaOH and 100 g of ice. The aqueous layer was extracted with $CH_2Cl_2$, and the combined organic layers were washed with water and satd. NaCl soln, dried and evaporated in vacuo to give the title compound.

B. trans 6(and 7)-Amino-5,6,7,8-tetrahydro-1,7(and 6)-naphthalenediol

A solution of 6,7-epoxy-5,6,7,8-tetrahydro-1-naphthol $O'$-benzyl ether 12.6 g (0.05 mole) in 200 ml dioxane was heated to 40° and a solution of sodium azide (6.8 g, 0.11 mole) in water (20 ml) was added dropwise. The mixture was heated under reflux overnight, cooled, filtered and the solvent was removed in vacuo.

The crude azide was dissolved in 100 ml of ether and added to a suspension of LAH (5 g) in 250 ml of ether. After several hours at reflux, the mixture was decomposed with aqueous potassium carbonate and the filtrate freed of solvent.

C. C-Phenylimidazole derivative of 6-Amino-5,6,7,8-tetrahydronaphthalene-1,7-diol $O'$-benzyl ether The trans amino alcohol was converted to its N-benzoyl derivative with benzoyl chloride-pyridine. This is added portionwise to excess thionyl chloride and then kept at 50°-60° for 3 hrs. Removal of excess reagent in vacuum leaves the crude cis oxazoline as its HCl salt, which is recrystallized from ethanol-ether.

EXAMPLE 16

Aminooxazoline derivative of 6(and 7)amino-5,6,7,8-tetrahydronaphthalene-1,7(and 6)diol An intimate mixture of 12.6 g (0.05 mole) of 6,7-epoxy-5,6,7,8-tetrahydro-1-naphthyl benzyl ether and 25 g of guaniline are heated to 140°-180° C until gas evolution ceases. The reaction mixture is cooled, and the product recrystallized from alcohol.

EXAMPLE 17

1,7(and 6)Dihydroxy-5,6,7,8-tetrahydro-6(and 7)naphthaleneacetic acid lactone

A solution of 12.6 g (0.05 mole) of 6,7-epoxy-5,6,7,8-tetrahydronaphthol benzyl ether and 7.5 g (0.05 mole) of diethylmalonate in 150 ml of absolute ethanol containing about 0.01 mole of sodium ethoxide was brought to reflux for several hours. The mixture was cooled, treated with concentrated HCl and warmed to effect hydrolysis and decarboxylation. Removal of solvent left crude lactone which was purified by chromatography on silica gel.

Catalytic debenzylation over 5% Pd on C in ethanol provided the free phenol.

EXAMPLE 18

7(and 6)Mercapto-1-hydroxy-5,6,7,8-tetrahydronaphthalene acetic acid lactone

Employing 6,7-epithio-5,6,7,8-tetrahydronaphthol benzyl ether in place of the epoxide in Example 17 produced the title compound.

What is claimed is:

1. A compound having the structure:

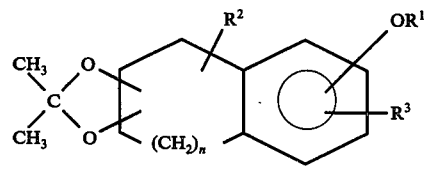

wherein $R^1$ is hydrogen, aryl-lower alkyl, or acyl; $R^2$ is hydrogen, lower alkyl, or aryl-lower alkyl; $R^3$ is hydrogen, acyl, lower alkyl, aryl-lower alkyl, lower alkoxy having up to 8 carbon atoms, carboxy, halo, alkenyl having 3 to 8 carbon atoms, nitro, cycloalkyl having 3 to 6 carbon atoms, amino, acylamino, $R^2O(CH_2)_n2$ wherein $R^2$ is as defined above, and $n^2$ is 0, 1 or 2, or dihydroxy-lower alkyl; and $n$ is 0, 1 or 2; wherein the term lower alkyl refers to alkyl groups having up to 8 carbon atoms; wherein the term acyl refers to acyl groups derived from carboxylic acids having up to 15 carbon atoms; and wherein the term aryl refers to phenyl or phenyl substituted with lower alkyl, halogen, nitro or methoxy.

2. A compound in accordance with claim 1 having the structure:

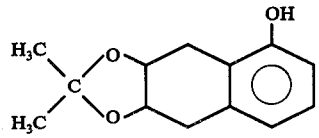

UNITED STATES PATENT OFFICE
CERTIFICATE OF CORRECTION

Patent No. 4,082,773          Dated April 4, 1978

Inventor(s) Frederic Peter Hauck

It is certified that error appears in the above-identified patent and that said Letters Patent are hereby corrected as shown below:

Abstract page, column 1, in the structure "n' " should read $--n^1--$.
Column 1, in the first structure "n' " should read $--n^1--$.
Column 2, lines 17 and 18, "suchas" should read --such as--.
Column 6, in structure X, "$OCH_2CH_5$" should read --$OCH_2C_6H_5$--.
Column 9, line 60, "wellknown" should read --well-known--.
Column 13, line 67, "bychromatography" should read --by chromatography--.
Column 14, line 47, after "diol" insert --of part B (0.1 m) in 200 ml of THF is treated with 1.7 g. (0.1 m) of--.

Signed and Sealed this

Twenty-fifth Day of July 1978

[SEAL]

Attest:

RUTH C. MASON
Attesting Officer

DONALD W. BANNER
Commissioner of Patents and Trademarks